United States Patent [19]

Martin

[11] 4,107,444
[45] Aug. 15, 1978

[54] THERMALLY STABLE, RIGID, ALIPHATIC DIOLS

[75] Inventor: Elmore Louis Martin, Wilmington, Del.

[73] Assignee: E. I. Du Pont de Nemours and Company, Wilmington, Del.

[21] Appl. No.: 751,085

[22] Filed: Dec. 16, 1976

[51] Int. Cl.$^2$ ............................................. C07C 31/18
[52] U.S. Cl. ................................. 568/807; 560/100; 560/102; 560/105; 568/811; 568/814
[58] Field of Search ......................... 260/618 R, 618 F

[56] References Cited

U.S. PATENT DOCUMENTS

| | | | |
|---|---|---|---|
| 2,924,622 | 2/1960 | Haven | 260/618 R |
| 2,967,854 | 1/1961 | Bungs | 260/618 R |
| 3,200,152 | 8/1965 | Ruppert et al. | 260/618 R |
| 3,240,722 | 3/1966 | Orttung et al. | 260/618 R |
| 3,284,511 | 11/1966 | Rowland et al. | 260/618 R |
| 3,422,143 | 1/1969 | Bottomley | 260/618 R |
| 3,622,636 | 11/1971 | Krimm et al. | 260/618 R |
| 3,867,465 | 2/1975 | Houlihan et al. | 260/618 R |
| 3,953,525 | 4/1976 | Anderson | 260/618 R |
| 4,035,427 | 7/1977 | Madelson | 260/618 R |

*Primary Examiner*—Norman Morgenstern

[57] ABSTRACT

Thermally stable, rigid, aliphatic diols of the formula

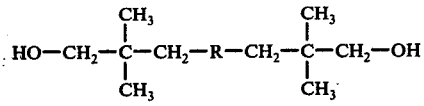

where R is a substituted or unsubstituted arylene group are useful as intermediates for forming polymers such as thermally stable, rigid polyesters.

8 Claims, No Drawings

THERMALLY STABLE, RIGID, ALIPHATIC DIOLS

BACKGROUND OF THE INVENTION

1. Field of the Invention

This invention relates to thermally stable, rigid, aliphatic diols, and more particularly to aromatic-aliphatic diols containing no hydrogen atoms beta to the hydroxyl groups.

2. Description of the Prior Art

Neopentyl glycol is known and polyesters have been made from this glycol. No aromatic neopentyl glycol is known.

SUMMARY OF THE INVENTION

There have now been discovered thermally stable, rigid, aliphatic diols of the formula

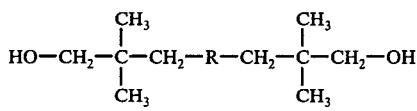

where R is an arylene selected from the group consisting of 1,4-phenylenes, 3,3'-biphenylenes, 4,4'-biphenylenes and 2,6-naphthylenes, said arylene being unsubstituted or substituted with halo, lower alkyl or phenyl.

The term "rigid" is used to denote the presence of one or more aromatic rings in the backbone between the hydroxyl groups. The term "halo" is intended to include chloro, bromo, fluoro and iodo. The term "lower alkyl" is intended to include alkyls of 1 to 6 carbons. The substituted phenylene may have 1 to 4 of the specified substituents, the substituted biphenylene may have 1 to 8 of these substituents, and the substituted naphthylene may have 1 to 6 of these substituents.

DESCRIPTION OF THE PREFERRED EMBODIMENT

The thermally stable, rigid, aliphatic diols of this invention are prepared by reacting a lower alkyl isobutyrate such as methyl isobutyrate with an α,α'-dibromoaromatic compound such as α,α'-dibromo-p-xylene in the presence of the reaction product of the lower alkyllithium such as n-butyllithium with a hindered secondary amine such as diisopropylamine to form a 1,4-bis(2-carbomethoxy-2-methylpropyl)benzene in accordance with the equation:

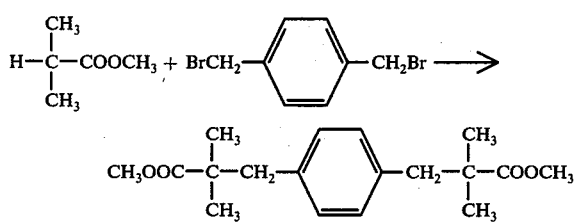

This product is then reduced with lithium aluminum hydride to form the product of the invention in accordance with the equation:

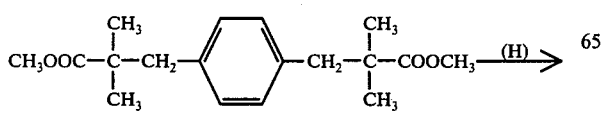

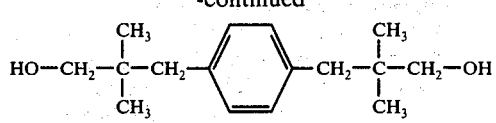

The various different arylene groups are obtained by substituting a different α,α'-dibromo aromatic compound for the α,α'-dibromo-p-xylene. Suitable α,α'-dibromo aromatic compounds include α,α'-dibromo-p-xylene
α,α'-dibromo-p,p'-bitolyl
2,6-bis(bromomethyl)naphthylene
α,α'-dibromo-2-chloro-p-xylene
α,α'-dibromo-2-methyl-p-xylene
α,α',2-tribromo-p-xylene
2,5-bis(bromomethyl)biphenyl
4,4'-bis(bromomethyl)-3,3'-difluorobiphenyl
3,6-bis(chloromethyl)durene
3,3'-dichloro-4,4'-bis(bromomethyl)biphenyl
1,5-dichloro-2,6-bis(bromomethyl)naphthylene
1-chloro-2,6-bis(bromomethyl)naphthylene
α,α'-dibromo-m,m'-bitolyl and the like.

The rigid diols of this invention are useful as intermediates for the preparation of polymers. For example, these diols could be end capped with an amino acid such as p-aminobenzoic acid to form an aromatic diamine which is useful for preparing thermally stable, rigid polyamides. These diols are also useful as the diol component for preparing thermally stable, rigid polyesters with aromatic diacids such as terephthalic acid as described by A. H. Frazer in U.S. application Ser. No. 751,087, filed on even date, now U.S. Pat. No. 4,065,431.

EXAMPLES OF THE INVENTION

The following examples illustrate the preparation of the thermally stable, aliphatic diols of this invention and their use in the preparation of thermally stable, rigid polyesters. In the examples the following tests and designations were employed.

Polymer melt temperature (PMT) is that temperature at which a fresh polymer sample leave a wet molten trail when stroked with moderate pressure across a clean, heated metal surface. A temperature-gradient bar covering the range of 50°–400° C was used for this determination (Beaman and Cramer, J. Polymer Sc., XXI, page 227).

Inherent viscosity was determined at 0.5% concentration and 30° C in a 40/60 weight mixture of 1,1,2,2-tetrachloroethane and phenol.

The standard fiber test designation T/E/Mi refers to tensile strength in grams per denier, elongation in percent, and initial modulus in grams per denier.

Orientation angle was determined by the method described by Kwolek in U.S. Pat. No. 3,671,542 at Column 20, lines 8–14.

EXAMPLE 1

Part A

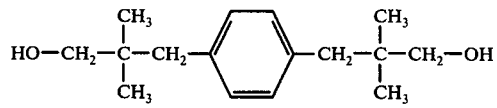

To 1 liter of dry tetrahydrofuran was added 52 g of diisopropylamine. The mixture was cooled to −78° C and 325 ml of 1.6 M n-butyllithium in hexane was added. After 1 hour of stirring 50 g of methyl isobutyrate was added dropwise followed by stirring for another 30 minutes. Then 63 g of α,α′-dibromo-p-xylene was slowly added. The reaction mixture was stirred overnight and brought to room temperature. The mixture was filtered and solvent was removed from the filtrate by evaporation. The residue was recrystallized from methanol to obtain 63 g of 1,4-bis(2-carbomethoxy-2-methylpropyl)benzene, m.p. 74°–76° C.

To 500 ml of dry tetrahydrofuran was added 11.4 g of lithium aluminum hydride and 60 g of 1,4-bis(2-carbomethoxy-2-methylpropyl)benzene. The mixture was stirred overnight at room temperature. To the thick reaction mixture was added 300 ml of ethyl acetate, 30 ml of saturated aqueous NH₄Cl, and 5 ml of concentrated HCl. The mixture was stirred and filtered. Solvent was evaporated from the filtrate and the residue was recrystallized from benzene to obtain 20 g of 1,4-bis(3-hydroxy-2,2-dimethylpropyl)benzene. The solid from the above filtration was slurried with 50 ml of H₂O, 20 ml of concentrated HCl, and 150 ml of benzene and heated at reflux for 1 hour. The benzene layer was then separated, dried over MgSO₄ at 80° C, filtered hot and then cooled to precipitate an additional 10 g of 1,4-bis(3-hydroxy-2,2-dimethylpropyl)benzene, m.p. 104°–105° C.

Part B

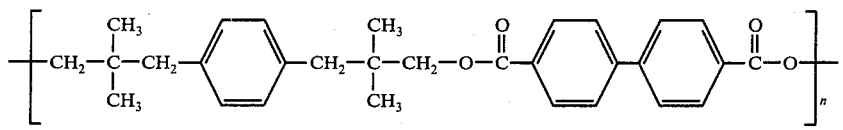

To a glass reactor with a nitrogen bleed and sidearm was added 0.048 g of tetraisopropyl titanate, 10.14 g (0.0406 mole) of 1,4-bis(3-hydroxy-2,2-dimethylpropyl)benzene, and 15.76 g (0.04 mole) of diphenyl bibenzoate. The resulting mixture, under nitrogen at atmospheric pressure, was heated for 18 hr at 220° C and 3 hr at 275° C, followed by 3 hr at 275° C at less than 0.05 mm Hg pressure. The resulting poly[oxycarbonyl(1,1′-biphenyl)-4,4′-diylcarbonyloxy(2,2-dimethyl-1,3-propanediyl) (1,4-phenylene)(2,2-dimethyl-1,3-propanediyl)] had a polymer melt temperature above 400° C, an inherent viscosity of 2.20 and was amorphous by X-ray diffraction.

Part C

Polymer from Part B was spun at a spinneret temperature of 350°–375° C at a pressure of 1600 psi, and the fiber was wound up at 200 yd/min. The fiber, after drawing at 3.0X at 150° C and heating at 200° C under restrained conditions at less than 0.01 mm Hg pressure for 18 hr, had a T/E/Mi at room temperature of 12/4/265, a T/E/Mi at 150° C of 7/5/75, an orientation angle of 10°, and was highly crystalline by X-ray diffraction.

Part D.

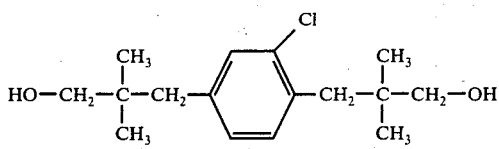

When α,α′-dibromo-2-chloro-p-xylene is substituted for α,α′-dibromo-p-xylene in the procedure of Part A above, the diol obtained is 1,4-bis(3-hydroxy-2,2-dimethylpropyl)-2-chlorobenzene.

Part E

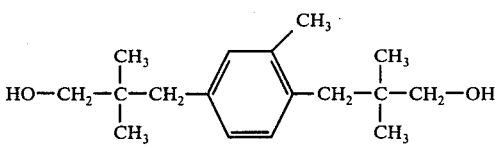

When α,α′-dibromo-2-methyl-p-xylene is substituted for α,α′-dibromo-p-xylene in the procedure of Part A, the diol obtained is 1,4-bis(3-hydroxy-2,2-dimethylpropyl)-2-methylbenzene.

Part F

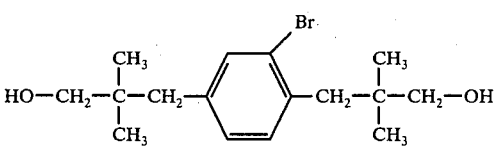

When α,α′,2-tribromo-p-xylene, prepared according to Hazlet et al., J. Org. Chem., 29, 2034 (1964), is substituted for α,α′-dibromo-p-xylene in the procedure of Part A above, the diol obtained is 1,4-bis(3-hydroxy-2,2-dimethylpropyl)-2-bromobenzene.

Part G

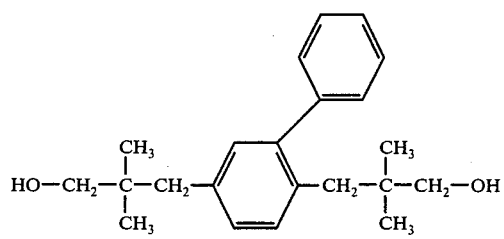

When 2,5-bis(bromomethyl)biphenyl is substituted for α,α′-dibromo-p-xylene in the procedure of Part A above, the diol obtained is 2,5-bis(3-hydroxy-2,2-dimethyllpropyl)-biphenyl.

EXAMPLE 2

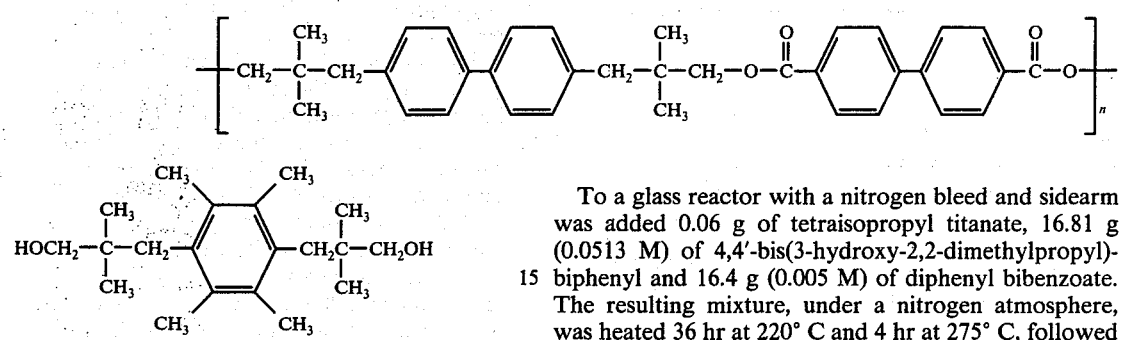

The procedure of Example 1, Part A, was repeated except that 3,6-bis (chloromethyl)durene was substituted for α,α'-dibromo-p-xylene. The diol obtained was 1,4-bis-(2,2-dimethyl-3-hydroxypropyl)tetramethylbenzene (m.p. = 147.5°–149° C, from methanol).

Anal. Calcd. for $C_{20}H_{34}O_2$: C, 78.38; H, 11.18. Found: C, 78.76; H, 11.24. 78.98 11.16.

The infrared spectrum (KBr) contained an OH stretch band at 2.98 μ.

EXAMPLE 3

Part A

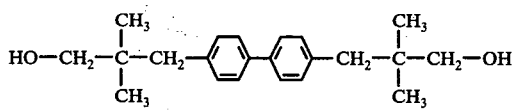

To 900 ml of dry tetrahydrofuran was added 42.0 ml of diisopropylamine. The mixture was cooled to −78° C and 195 ml of 1.6 M n-butyllithium in hexane was added. After 1 hr of stirring 30.5 g of methyl isobutyrate was added dropwise followed by an additional 30 minutes of stirring. A solution of 51 g of α,α'-dibromo-p,p'-bitolyl in 300 ml of dry tetrahydrofuran was added dropwise. The mixture was stirred overnight and brought to room temperature. Tetrahydrofuran was removed by evaporation. The residue was dissolved in 300 ml of methylene chloride and washed twice with 300 ml of water. To the milky liquid was added 235 ml of tetrahydrofuran and the water separated out. The organic layer was dried and evaporated to dryness to obtain about 60 g of yellow liquid which crystallized on standing. Drying yielded 48 g of 4,4'-bis(2-carbomethoxy-2-methylpropyl)biphenyl, m.p. 68–70° C.

To a solution of 5.94 g of lithium aluminum hydride in 1500 ml of dry tetrahydrofuran 30 g of 4,4'-bis(2-carbomethoxy-2-methylpropyl)biphenyl was slowly added. The reaction mixture thickened on stirring overnight. Then there was added 150 ml of ethyl acetate, 60 ml of saturated aqueous $NH_4Cl$ and 150 ml of concentrated HCl After thorough mixing, the solid and liquid were separated by filtration. The filtrate was evaporated to dryness and the residue recrystallized from benzene to obtain 15 g of 4,4'-bis(3-hydroxy-2,2-dimethylpropyl)biphenyl. The solid from the above filtration was slurried with 50 ml of $H_2O$, 10 ml of concentrated HCl and 50 ml of benzene and the mixture heated at reflux for 1 hr. The benzene layer was separated, dried with $MgSO_4$ at 80° C, filtered hot and then cooled to precipitate an additional 10 g of 4,4'-bis(3-hydroxy-2,2-dimethylpropyl)biphenyl, m.p. 168°–170° C.

Part B

To a glass reactor with a nitrogen bleed and sidearm was added 0.06 g of tetraisopropyl titanate, 16.81 g (0.0513 M) of 4,4'-bis(3-hydroxy-2,2-dimethylpropyl)biphenyl and 16.4 g (0.005 M) of diphenyl bibenzoate. The resulting mixture, under a nitrogen atmosphere, was heated 36 hr at 220° C and 4 hr at 275° C, followed by 3 hr at 275° C at less than 0.05 mm Hg pressure. The resulting poly[oxycarbonyl(1,1'-biphenyl)-4,4'-diylcarbonyloxy(2,2-dimethyl-1,3-propanediyl) (1,1'-biphenyl)-4,4'-diyl(2,2-dimethyl-1,3-propanediyl)] had a PMT of approximately 400° C, an inherent viscosity of 1.10, and showed low crystallinity by X-ray diffraction.

Part C

The polymer from Part B was spun at a spinneret temperature of 350°–375° C and the fiber was wound up at 500 yd/min. The fiber, after being drawn 4.0 times at 180° C, had an orientation angle of 13°, was medium crystallinity, had a T/E/Mi at room temperature of 11/5/262 and a T/E/Mi at 150° C of 8/5/150.

Part D

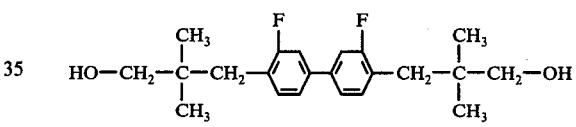

When 4,4'-bis(bromomethyl)-3,5'-difluorobiphenyl (prepared by coupling 2-fluoro-4-iodotoluene followed by bromination) is substituted for α, α'-dibromo-p,p'-bitolyl in the procedure of Part A above, the diol obtained is 4,4'-bis(3-hydroxy-2-2-dimethylpropyl)-3,3'-difluorobiphenyl. Example 4

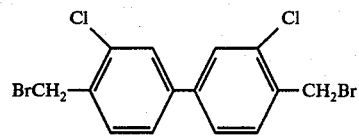

In a 2-liter flask equipped with a reflux condenser capped with a nitrogen bubbler was placed 83.7 g of 3,3'-dichloro-4,4'-bitolyl, 121.5 g of N-bromosuccinimide, 4.0 g of benzoyl peroxide, 630 ml of carbon tetrachloride, and a few boiling chips. The mixture was refluxed for 21½ hours and cooled to room temperature. Four grams of benzoyl peroxide was added and reflux was continued for 8 hours. The mixture was filtered hot and the solid was rinsed on the filter with 500 ml of hot carbon tetrachloride. Cooling the combined filtrate and rinsings gave 75.5 g of crude 3,3'-dichloro-4,4'-bis(-bromomethyl)biphenyl melting at 148°–154° C. A recrystallization from chloroform raised the melting point to 159°–161° C.

Anal. Calcd. for $C_{14}H_{10}Cl_2Br_2$: C, 41.11; H, 2.47; Br, 39.08; Cl, 17.34. Found: C, 41.27; H, 2.68; Br, 38.62; Cl, 17.23. 41.12 2.57 38.58 17.26

Part B

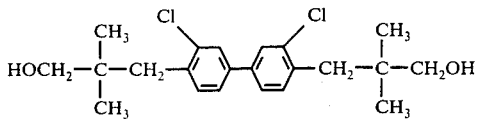

The procedure of Example 3, Part A, was repeated except that 3,3'-dichloro-4,4'-bis(bromomethyl)biphenyl was substituted for α,α'-dibromo-p,p'-bitolyl. The diol obtained was 3,3'-dichloro-4,4'-bis(3-hydroxy-2,2-dimethylpropyl)biphenyl (m.p. = 134.75–135.75° C from chloroform).

Anal. Calcd. for $C_{22}H_{28}Cl_2O_2$: C, 66.83; H, 7.14; Cl, 17.94. Found: C, 66.86; H, 6.73; Cl, 17.40. 66.78 7.01 17.89

The infrared spectrum (KBr) contained an OH stretch band at 3.00 μ.

EXAMPLE 5

The procedure of Example 3, Part A, was repeated except that α,α'-dibromo-m,m'-bitolyl was substituted for α,α'-dibromo-p,p'-bitolyl. The diol obtained was 3,3'-bis(3-hydroxy-2,2-dimethylpropyl)biphenyl (m.p. = 104°–105.25° C after recrystallization from a mixture of methanol and water).

Anal. Calcd. for $C_{22}H_{30}O_2$: C, 80.93; H, 9.26. Found: C, 80.54; H, 8.97 80.15 9.16 80.49 9.25.

The infrared spectrum (KBr) contained an OH stretch band at 2.97 μ.

EXAMPLE 6

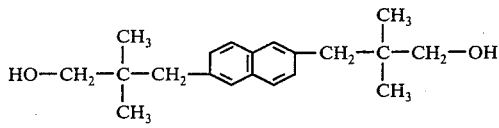

To a solution of 56 ml of diisopropylamine in 1200 ml of dry tetrahydrofuran at −78° C was added 260 ml of 1.6 M n-butyllithium in hexane. After 1 hr of stirring 40.4 g of methyl isobutyrate was added dropwise and the solution stirred for another 30 minutes. A 60-g portion of 2,6-bis(bromomethyl)naphthalene was added slowly, and the reaction mixture was stirred overnight and then brought to room temperature. Tetrahydrofuran was removed by evaporation. The residue was dissolved in 300 ml of chloroform, washed 3 times with 400 ml of $H_2O$, dried and evaporated to dryness to obtain 56 g of 2,6-bis(2-carbomethoxy-2-methylpropyl)naphthalene, m.p. 108° C–110° C. The product was recrystallized from benzene.

To a solution of 6.0 g of lithium aluminum hydride in 1 liter of dry tetrahydrofuran, 40 g of 2,6-bis(2-carbomethoxy-2-methylpropyl)naphthalene was added slowly. The reaction mixture thickened on stirring overnight. Then there was added 150 ml of ethyl acetate, 60 ml of saturated aqueous $NH_4Cl$ and 150 ml of concentrated HCl. After thorough mixing the solid and liquid were separated by filtration. The filtrate was evaporated to dryness and the residue was recrystallized from benzene to obtain about 20 g of 2,6-bis(3-hydroxy-2,2-dimethylpropyl)naphthalene. The solid from the above filtration was slurried with 50 ml of $H_2O$, 10 ml of concentrated HCl and 50 of benzene and the mixture heated at reflux for 1 hr. The benzene layer was separated, dried with $MgSO_4$ at 80° C, filtered hot and then cooled to precipitate about 10 g of 2,6-bis(3-hydroxy-2,2-dimethylproply)naphthalene, m.p. 162°–165° C.

Part B

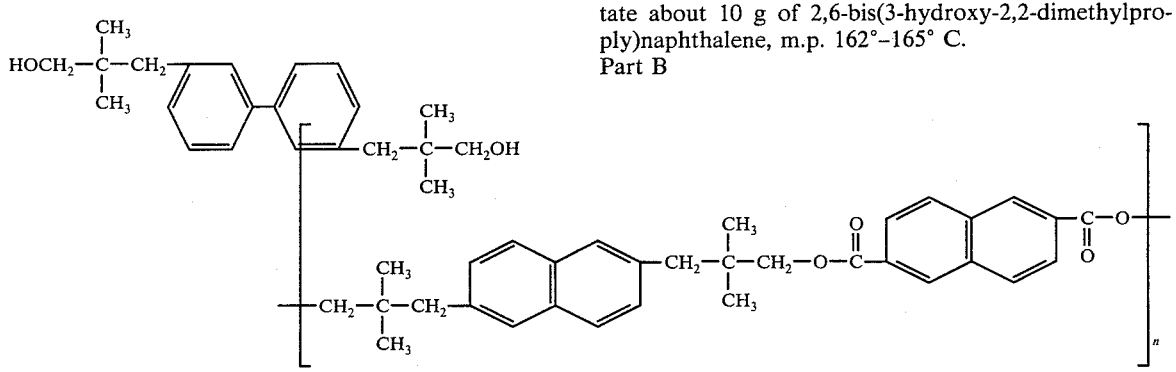

A mixture of 0.006 g of tetraisopropyl titanate, 1.521 g (0.0051 M) of 2,6-bis(3-hydroxy-2,2-dimethylpropyl)-naphnthalene and 1.840 g (0.005 M) of diphenyl 2,6-naphthalenedicarboxylate was polymerized using the procedure of Example 3, Part B. The resulting poly[oxycarbonyl(2,6-naphthalene )diylcarbonyloxy(2,2-dimethyl-1,3-propanediyl)-(2,6-naphthalene)diyl(2,2-dimethyl-1,3-propanediyl)] had a PMT of approximately 400° C, an inherent viscosity of 1.10, and showed trace crystallinity by X-ray diffraction.

Part C

The polymer from Part B was spun at a spinneret temperature of 350°14 375° C and the fiber was wound up at 500 yd/min. The fiber, after being drawn 3.5 times at 170° C, had an orientation angle of 14°, was of medium crystallinity, had a T/E/Mi at room temperature of 9/5/260 and a T/E/Mi at 150° C of 6/5/148.

EXAMPLE 7

Part A

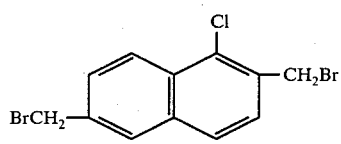

In a 1-liter flask equipped with a reflux condenser capped with a nitrogen T-tube was placed 41.0 g of 1-chloro-2,6-dimethylnaphthalene, 80 g of N-bromosuccinimide, 0.20 g of benzoyl peroxide, 475 ml of carbon tetrachloride and a few boiling chips. The mixture was refluxed for three hours and cooled to room temperature. After 0.30 g of α,α'-azobis(isobutyronitrile) was added, refluxing was continued for 17½ hours. After the mixture had been cooled to room temperature, it was filtered. The solid was rinsed on the filter with carbon tetrachloride and dried. Stirring of this solid with 500 ml of water for 2 hours, followed by filtration, rinsing of the solid on the filter with water, and drying, yielded 30.30 g of crude 1-chloro-2,6-bis(bromomethyl)naphthalene melting at 127°–129° C.

The filtrate from the first filtration was evaporated to 100 ml and refrigerated for several hours. Filtration of the resulting solid, rinsing on the filter with carbon tetrachloride, and drying yielded another 23.80 g of crude 1-chloro-2,6-bis(bromomethyl)naphthalene melting at 120°–128° C. Recrystallization of the combined products fom chloroform raised the melting point to 131°–133° C.

Anal. Calcd. for C₁₂H₉Br₂Cl: C, 41.36; H, 2.60; Br, 45.87; Cl, 10.18. Found: C, 40.28; H, 2.51; Br, 46.96; Cl, 10.53 40.22 2.52 46.79 10.52

Part B

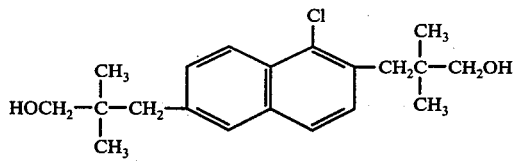

The procedure of Example 6, Part A, was repeated except that 1-chloro-2,6-bis(bromomethyl)naphthylene was substituted for 2,6-(bromomethyl)naphthalene. The diol obtained was 1-chloro-2,6-bis(3-hydroxy-2,2-dimethylpropyl)-naphthalene (m.p. = 144°–145.5° C).

EXAMPLE 8

Part A

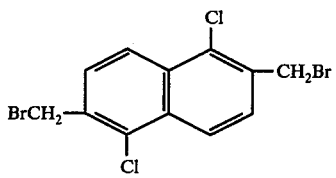

In a 250-ml flask equipped with a reflux condenser capped with a nitrogen T-tube was placed 12.10 g of 1,5-dichloro-2,6-dimethylnaphthalene, 20 g of N-bromosuccinimide, 0.10 g of benzoyl peroxide, 120 ml of carbon tetrachloride and a few boiling chips. The mixture was refluxed for 3 hours and cooled to room temperature. After 0.20 g of α,α'-azobis(isobutyronitrile) was added, refluxing was continued for 16½ hours. After the mixture had cooled to room temperature, the precipitated solid was filtered, rinsed on the filter with carbon tetrachloride and dried. Stirring of this solid for 2½ hours with 400 ml of water, followed by filtration and drying of the solid on the filter, gave 14.03 g of crude 1,5-dichloro-2,6-bis(bromomethyl)naphthalene melting at 219°–221° C. Recrystallization from refluxing toluene raised the melting point to 221°–222.5° C.

Anal. Calcd. for C₁₂H₈Br₂Cl₂: C, 37.64; H, 2.10; Br, 41.74; Cl, 18.52. Found: C, 38.11; H, 2.27; Br, 42.40; Cl, 18.04. 38.10 2.21 42.24 18.12.

Part B

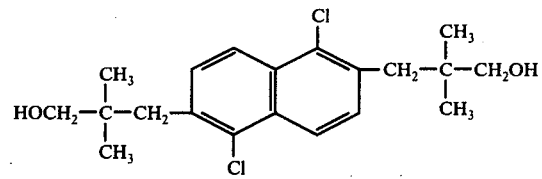

The procedure of Example 6, Part A, was repeated except that 1,5-dichloro-2,6-bis(bromomethyl)naphthalene was substituted for 2,6-bis(bromomethyl)naphthalene. The diol obtained was 1,5-dichloro-2,6-bis(3-hydroxy-2,2-dimethylpropyl)naphthalene (m.p. = 213-3/4-214-3/4° C, from alcohol).

Anal. Calcd. for C₂₀H₂₆Cl₂O₂: C, 65.04; H, 7.10; Cl, 19.20. Found: C, 65.31; H, 7.14; Cl, 18.91. 64.85 7.16 18.99 64.95 7.28

The infrared spectrum (KBr) contained an OH stretch band at 300 μ.

I claim:

1. Thermally stable, rigid, aliphatic diols of the forumla

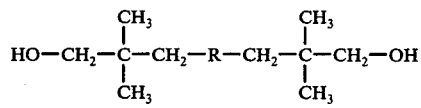

where R is an arylene selected from the group consisting of 1,4-phenylenes, 3,3'-biphenylenes, 4,4'-biphenylenes and 2,6-naphthylenes, said arylene being unsubstituted or substituted with halo, lower alkyl or phenyl.

2. The diols of claim 1 in which R is 1,4-phenylene or substituted 1,4-phenylene.

3. The diol of claim 2 of the formula

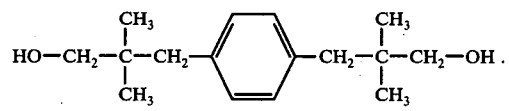

4. The diols of claim 1 in which R is 4,4'-biphenylene or substituted 4,4'-biphenylene.

5. The diol of claim 4 of the formula

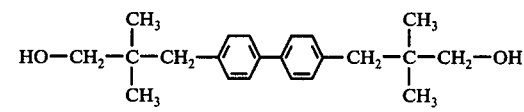

6. The diols of claim 1 in which R is 2,6-naphthylene or substituted 2,6-naphthylene.

7. The diol of claim 6 of the formula

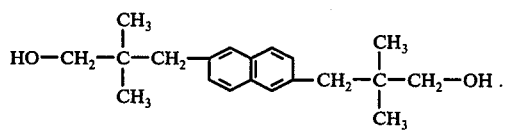

8. The diol of claim 1 of the formula

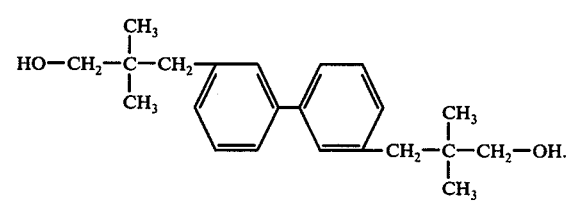

* * * * *